United States Patent
Lin et al.

(10) Patent No.: US 6,777,247 B2
(45) Date of Patent: Aug. 17, 2004

(54) NERVOUS NECROSIS VIRUS PROTEIN

(75) Inventors: Han-You Lin, Taipei (TW); Tsun-Yung Kuo, Taipei (TW); Hsiao-I Huang, Arcadia, CA (US); Huey-Lang Yang, Tenafly, NJ (US)

(73) Assignee: Academia Sinica, Taipei (TW)

( * ) Notice: Subject to any disclaimer, the term of this patent is extended or adjusted under 35 U.S.C. 154(b) by 231 days.

(21) Appl. No.: 09/867,932

(22) Filed: May 30, 2001

(65) Prior Publication Data
US 2003/0049825 A1 Mar. 13, 2003

(51) Int. Cl.[7] .................................................. A61K 39/12
(52) U.S. Cl. .................. 436/547; 424/186.1; 424/204.1
(58) Field of Search ....................... 436/547; 424/186.1, 424/204.1

(56) References Cited

PUBLICATIONS

Dagan et al., Mol. Biol. Evol. 19(7):1022–1025, 2000.*

Mori et al., "Properties of a New Virus Belonging . . . ", Virology, vol. 187, No. 1, Mar. 1992;368–371.

Nishizawa et al., "Comparison of the coat protein genes of five fish . . . ", J.Gen. Virology, vol. 76, part 7, 1995;1563–1569.

* cited by examiner

*Primary Examiner*—Laurie Scheiner
(74) *Attorney, Agent, or Firm*—Fish & Richardson P.C.

(57) ABSTRACT

The invention relates to a new RNA polymerase isolated from a Nervous Necrosis Virus.

12 Claims, 2 Drawing Sheets

NERVOUS NECROSIS VIRUS PROTEIN

BACKGROUND OF THE INVENTION

Nervous necrosis virus (NNV) is a major worldwide viral pathogen of several economically important fish species and can cause serious damage to the aquaculture industry. NNV infection can result in rapid and total death of fish fry in commercial hatcheries, and cause disease and high morality in hatchery-reared larvae and juveniles. Typical symptoms of infection include spiral swimming behavior just before death, and infection can be confirmed histopathologically by observing vacuoles in the retina and brain tissue.

NNV is classified as member of the Nodaviridae (see e.g., Mori et al., Virology 187:368–371, 1992). The NNV genome is composed of two (+) strand RNA molecules. RNA 1 is about 1.5 kb in length and encodes a structural coat protein, and RNA 2 is about 3 kb in length and encodes an RNA polymerase.

SUMMARY OF THE INVENTION

The invention is based on the discovery of a new coat encoded by the RNA 1 segment of an NNV isolate, and the discovery that this new NNV protein is useful as a capture antigen in an NNV detection assay and as an antigen in an NNV vaccine. The amino acid sequence of this NNV protein is shown below.

```
                                             (SEQ ID NO:2)
MVRKGEKKLAKPATTKAANPQPRRRANNRRRSNRTDAPVSKASTVTGFGR

GTNDVHLSGMSRISQAVLPAGTGTDGYVVVDATIVPDLLPRLGHAARIFQ

RYAVETLEFEIQPMCPANTGGGYVAGFLPDPTDNDHTFGALQATRGAVVA

KWWESRTVRPQYTRTLLWTSSGKEQRLTSPGRLILLCVGNNTDVVNVSVL

CRWSVRLSVPSLETPEETTAPIMTQGSLYNDSLSTNDSKSILLGSTPLDI

APDGAVFQLDRLLSIDYSLGTGDVDRAVYWHLKKFAGNAGTPAGWFRWGI

WDNFNKTFTDGVAYYSDEQPRQILLPVGTVCTRVDSEN
```

In the natural NNV isolate, this amino acid sequence is encoded by the nucleotide sequence shown below.

```
                                             (SEQ ID NO:1)
atggtacgcaaaggtgagaagaaattggcaaaaccgcgaccaccaaggc cgcgaatccgcaacccgccgacgtgctaacaatcgtcggcgtagtaatc gcactgacgcacctgtgtctaaggcctcgactgtgactggatttggacgt gggaccaatgacgtccatctctcaggtatgtcgagaatctcccaggccgt cctcccagccgggacaggaactgacggatacgttgttgttgacgcaacca tcgtccccgacctcctgccacgactgggacacgctgctagaatcttccag cgatacgctgttgaaacactggagtttgaaattcagccaatgtgccccgc aaacacgggcggtggttacgttgctggcttcctgcctgatccaactgaca acgaccacaccttcggcgcgcttcaagcaactcgtggtgcagtcgttgcc aaatggtgggaaagcagaacagtccgacctcagtacacccgcacgctcct ctggacctcgtcgggaaaggagcagcgtctcacgtcacctggtcggctga tactcctgtgtgtcggcaacaacactgatgtggtcaacgtgtcggtgctg tgtcgctggagtgttcgactgagcgttccatctcttgagacacctgaaga gaccaccgctcccatcatgacacaaggttccctgtacaacgattccctat ccacaaatgactccaagtccatcctcctaggatccacgccactggacatt gccctgatggagcagtcttccagctggaccgtctgctgtccattgacta cagccttggaactggagatgttgaccgtgctgtttactggcacctcaaga agtttgctggaaatgctggcacacctgcaggctggtttcgctggggcatc tgggacaacttcaacaagacgttcacagatggcgttgcctactactctga tgagcagccccgtcaaatcctgctgcctgttggcactgtctgcaccaggg ttgactcggaaaac.
```

Accordingly, the invention features a substantially pure polypeptide including an amino acid sequence at least 99% (e.g., 100%) identical to the amino acid sequence of SEQ ID NO:2. In some embodiments, the polypeptide can include the amino acid sequence of SEQ ID NO:2, with up to 4 conservative amino acid substitutions, which would not be expected to affect the ability of the polypeptide to serve as a capture antigen in an NNV detection assay or as an antigen in an NNV vaccine (e.g., a subunit or DNA vaccine).

The invention further includes an isolated nucleic acid encoding a polypeptide of the invention, a vector including a nucleic acid of the invention, or a cultured host cell containing a nucleic acid of the invention.

In other aspects, the invention includes (1) a method of producing a polypeptide by culturing a cultured host cell of the invention in a culture, expressing the polypeptide in the cultured host cell, and isolating the polypeptide from the culture; (2) a method of detecting exposure of a fish to nervous necrosis virus by providing a serum sample from a fish, contacting the serum sample to a substrate coated with a polypeptide of the invention, and determining whether antibodies in the serum sample specifically bind to the polypeptide on the substrate, where antibodies specifically binding to the polypeptide on the substrate indicates that the fish has been exposed to the nervous necrosis virus; and (3) a method of eliciting an antibody response to a nervous necrosis virus in an animal (e.g., a fish) by administering a polypeptide, nucleic acid, or cell of the invention to an animal in an amount sufficient to elicit an antibody response to the nervous necrosis virus.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones: e.g., as these occur in a DNA library such as a cDNA or genomic DNA library.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

A "conservative amino acid substitution" is one in which an amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The "percent identity" of two amino acid sequences or of two nucleic acids is determined using the algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12. BLAST protein searches are performed with the XBLAST program, score=50, wordlength=3. Where gaps exist between two sequences, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used. See http://www.ncbi.nlm.nih.gov.

Other features or advantages of the present invention will be apparent from the following detailed description, and also from the claims.

DETAILED DESCRIPTION

Figure 1:
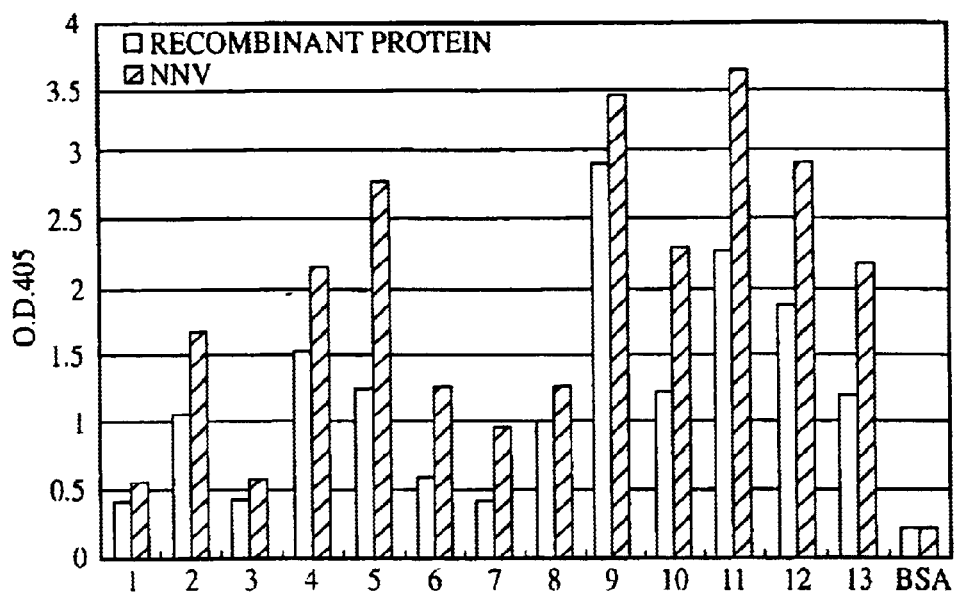
FIG. 1 is a bar graph showing the ELISA optical density for different grouper serum samples.

The invention relates to a new NNV structural protein and its variants, e.g., that can be used in NNV detection methods and NNV vaccines. Contemplated within the scope of the invention are NNV protein vaccines containing a polypeptide of the invention, and NNV nucleic acid (e.g., DNA) vaccines containing a nucleic acid or vector of the invention. Such vaccines can be administered to commercially valuable fish stock in an effort to reduce the costly consequences of NNV infection. Materials, procedures, and DNA vectors for expressing and isolating a cloned polypeptide are well within skill in the art of molecular biology, as shown in the Example below. In addition, vectors for expressing a polypeptide in fish are also known.

Without further elaboration, it is believed that one skilled in the art can, based on the above disclosure and the example below, utilize the present invention to its fullest extent. The following example is to be construed as merely illustrative of how one skilled in the art can isolate and use the polypeptides and nucleic acids of the invention, and are not limitative of the remainder of the disclosure in any way. Any publications cited in this disclosure are hereby incorporated by reference.

EXAMPLE

Materials and Methods

Purification of Viral RNA.

RNA was extracted using the method of Chomczynski et. al., Anal. Biochem. 162:156–159, 1087. All solutions were prepared using 0.1% DEPC (diethyl pyrocarbonate)-treated double-distilled water. RNA was extracted from NNV-infected fish tissue obtained locally at Pong Hu Island, Taiwan. The samples were homogenized in 500 $\mu$l of GTC Buffer (20 $\mu$l 3 M sodium acetate). To the homogenate was added 500 $\mu$l phenol (pH 4) and 150 $\mu$l chloroform. The resulting mixture was agitated for 1 minute. The mixture was then centrifuged for 20 minutes to separate the aqueous and organic components. The supernatant (aqueous layer) was then isolated. 0.7× of supernatant volume of isopropanol was then added to precipitate the nucleic acid. The precipitate was washed using ice cold ethanol and air dried. The nucleic acid was then dissolved in DEPC treated water.

Cloning and Sequencing.

cDNA synthesis was performed by random priming. The primed fragments were then subjected to PCR using two primers based on the sequence of the striped jack nervous necrosis virus coat protein gene (Nishizawa et al., J. Gen. Virol. 76:1563–1569, 1995). PCR reaction mixtures containing RNA, AMVRT buffer, RNAse inhibitor, dNTP, primers, and AMVRTase were incubated for 50 minutes at 42° C. for cDNA synthesis. PCR conditions were 94° C. for 1 minutes, 55° C. for 1 minute, and 72° C. for one minute; for 30 cycles. A 0.85 kb cDNA was then purified using the Nucleotide Removal Kit (Qiagen) to eliminate unincorporated substrates. The PCR product was subcloned into the pCR-Blunt plasmid (Invitrogen) and then sequenced.

The RACE cloning method (BRL) was then used to clone the complete open reading frame (1.2 kb) based on the 0.85 kb partial sequence. Again the starting material used for genome walking was the RNA extracted from the NNV infected fish tissue described above.

Expression and Purification of NNV Coat Protein.

The DNA fragment containing the full open reading frame of NNV RNA1 was cloned into the express vector pET24a (Novagen). The resulting plasmid was used to transformed E. coli BL-21. Protein expression was induced by IPTG and confirmed by SDS-PAGE of bacterial extracts. NNV coat protein was obtained as insoluble inclusions after IPTG induction. Inclusion bodies were solubilized, and the protein refolded in solution containing 50 mM 3-(cyclohexylamino)-1-propanesulfonic acid (CAPS; Research Organic, Inc.) at pH 11.0. The protein solution was then dialyzed against solution containing 20 mM Tris (pH 8.5) and 0.1 mM dithiothreitol to remove CAPS and purified using an ion-exchange (DEAE-Sepharose; Amersham Pharmacia) and then a gel filtration (Superose 12; Amersham Pharmacia) column.

Preparation of Rabbit Anti-Grouper Antibodies.

To facilitate detection of grouper antibodies, grouper immunoglobulin was prepared from serum and purified using a protein-A column (Pierce). The grouper immunoglobulin was injected into rabbits to produce anti-grouper antibodies. After two immunizations, rabbit serum was purified and conjugated with alkaline phosphatase (AP). This rabbit anti-grouper Ig-AP was used as secondary antibody for ELISA as described herein.

Preparation of Rabbit Anti-NNV Polyclonal Antiserum.

Virus particles were purified from tissue or suspension of cell cultures and concentrated using sucrose gradient ultracentrifugation. The amount of the viral protein in the concentrate was assayed using the BDT protein measurement kit (Pierce). A sample of the virus concentrate containing 300 μg of viral protein was diluted in PBS, mixed with equal volumes of Freund's complete adjuvant to a final volume of 100 μl, and then inoculated into 3-month old female New Zealand rabbits. After booster immunization on week 4 (post-inoculation) with Freund's incomplete adjuvant, the rabbits were bled at week 6. The serum from the bleed was titrated for anti-NNV serum antibodies, as measured by western blotting and ELISA.

Following the above procedure, rabbit antibodies against the recombinantly produced NNV coat protein as described above was produced.

ELISA.

Purified NNV virus particles and recombinant NNV coat protein were diluted to suitable volume with coating buffer (32 mM sodium carbonate, 68 mM sodium bicarbonate; pH 9.6) to achieve 0.5 μg/well of NNV or 1 μg/well of recombinant coat protein. The wells of a 96-well immuno module (Nunc) were coating at 4° C. overnight. The wells were then blocked with 5% skimmed milk powder in PBS at 37° C. for 1 hour.

Serum samples were diluted 1000× to a final concentration of about 200 μg per well and incubated in the coated wells at 37° C. for 1 hour. Wells were then washed three times with 200 μl TBS containing 0.5% Tween 20. A 10,000× dilution of the labeled rabbit anti-grouper secondary antibody was then added at 200 μl/well and incubated at 37° C. for 1 hour. The wells were washed as described above and developed with p-nitrophenyl phosphate at room temperature for 30 minutes. The $OD_{405}$ for each well was read in an ELISA reader.

NNV Coat Protein and NNV Particle Vaccine.

The vaccine was given at 20 μg/protein/fish by intraperitoneal injection at the midline of the ventral abdomen.

NNV DNA Vaccine.

An NNV coat protein DNA vaccine was produced by inserting the NNV coat protein gene into the pTracer-CMV (Invitrogen) vector, which contains a CMV promoter driving expression of an insert and a green fluorescent protein (GFP) reporter gene. The resulting plasmid was sequenced to confirm the success of construction. Plasmid mixed with PBS was the vaccine composition.

NNV Neutralization Assay.

Cells were suspended and placed in a well of a 96-well plate. The cells were incubated until they attached to the well bottom and grew to $5-7\times10^4$ cells per well. Sera were diluted with PBS. 100 $TCID_{50}$ of virus were incubated at room temperature for 1 hour before introduction into the wells containing cells. Four wells were tested for each dilution. Cytopathic effect was observed to three days thereafter. The neutralization titer was the last dilution resulting in cytopathic effect in at least two of the four wells after three days post-infection.

Results

The presence of NNV in the local grouper samples was confirmed by PCR using the method described in Nishizawa et al., J. Gen. Virol. 76:1563–1569, 1995. RNA was extracted from brain tissue and purified. The NNV coat protein gene was cloned and sequenced to obtain the nucleic acid encoding the coat protein (SEQ ID NO:1) and the predicted amino acid sequence of the coat protein (SEQ ID NO:2).

The recombinant protein and naturally occurring (native) viral protein was tested by Western blot analysis. The recombinant protein was recognized by antiserum generated by native NNV antigen, indicating that the recombinant protein maintained at least sufficient native protein structure for antibody recognition. SDS-PAGE indicated that the molecular weight of native and recombinant coat protein were similar, at about 42 kDa. In addition, antibodies generated in response to native or recombinant coat protein recognized both proteins in Western blots. Thus, the recombinant, bacterially produced protein retained the correct tertiary structure of the native viral coat protein.

To determine whether the coat protein can be used for detection or diagnosis of NNV in fish, recombinant NNV coat protein and native NNV virus particles were coated onto plastic wells and used as antibody capture antigens. Thirteen grouper serum samples randomly collected from a fish farm and a bovine serum albumin control sample were tested. The results are shown in FIG. 1 and indicate that recombinant coat protein can be used in ELISA.

Whether the recombinant NNV coat protein might be useful as a subunit vaccine was then determined. Ninety 2-inch long grouper fingerlings (about 2 months old) were used for protein vaccination (60 fish receiving recombinant vaccine, 15 fish receiving killed vaccine, and 15 fish receiving PBS negative control vaccine). Fifty negative control fish were injected with PBS mixed with a adjuvant corresponding to what was present in the other vaccines in the study. Another fifty fish were injected with inactivated NNV virus particles mixed with adjuvant. Lastly, sixty fishes were injected with recombinant protein mixed with adjuvant. Blood was collected from five randomly selected fish in each group at week 0 and week 4, and from all fishes at week 6 for each group.

Figure 2:
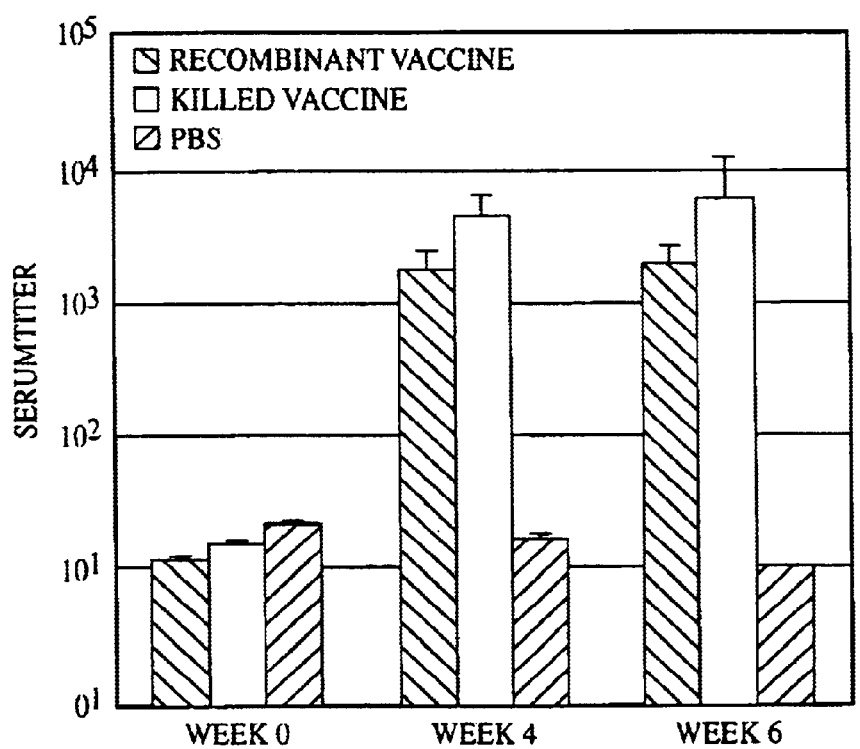
FIG. 2 is a bar graph showing ELISA titers for serum samples from groupers vaccinated with a polypeptide of the invention.
Figure 3:
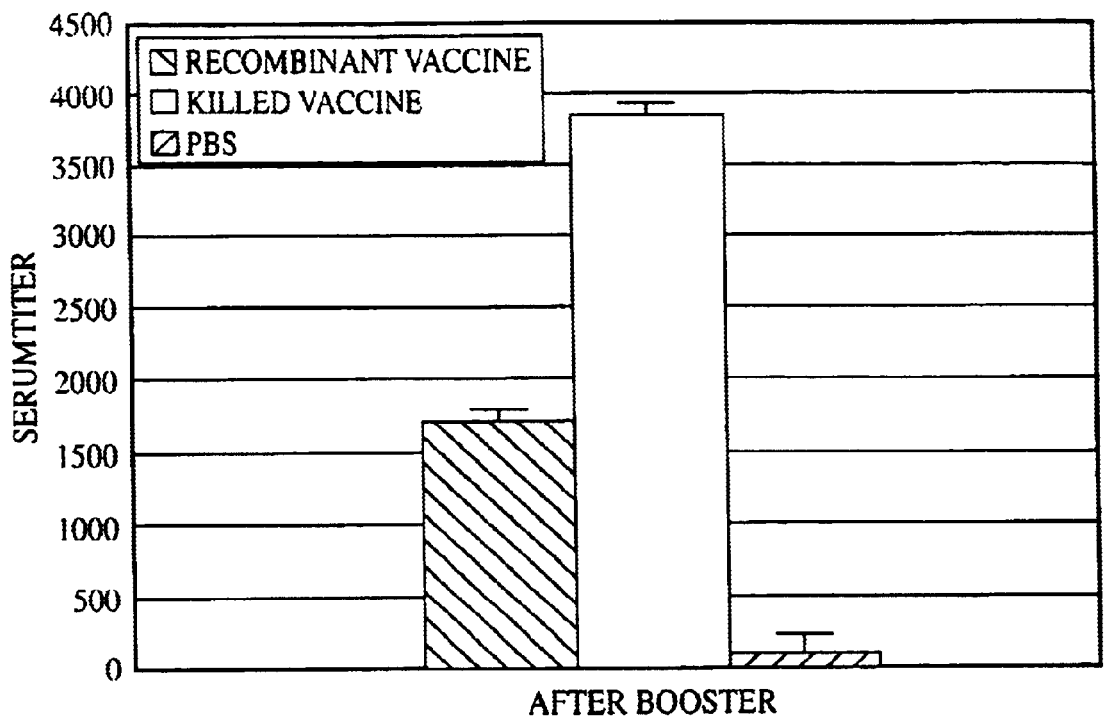
FIG. 3 is a bar graph showing the neutralization activity of serum samples from vaccinated fish.

Vaccine efficacy was measured by titrating serum NNV antibody and NNV neutralization activity in serum. Serum titer was analyzed by ELISA as described above, with NNV virus particles as capture antigen. Neutralizing antibody titers were assayed using serum collected after the booster. Five samples form the same group were pooled together for antibody and neutralization determinations. The antibody titers are shown in FIG. 2, and the neutralization titers are shown in FIG. 3.

The results indicate that NNV-specific antibody titers were detectable by week 4. Statistical analysis (ANOVA) indicated that antibody titers in both vaccine groups (recombinant coat protein and killed viral particles) were significantly higher than the negative control group (FIG. 2; $p<0.001$). Surprisingly, the neutralizing antibody titer in the fish receiving recombinant coat protein was far higher than the neutralizing titers in the fish receiving viral particles (FIG. 3). Since neutralizing activity is a far better surrogate for vaccine efficacy than total pathogen-specific antibody, these results indicate that subunit vaccines based on this recombinant NNV coat protein would be more efficacious than vaccines based on killed viral particles.

Figure 4:
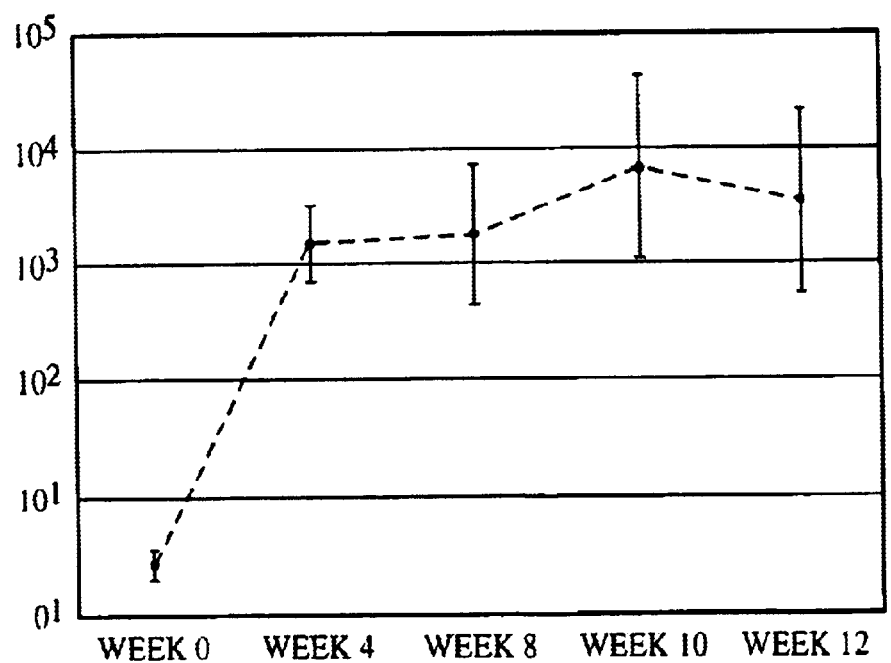
FIG. 4 is a line graph showing NNV antibodies in mice injected with a DNA vaccine encoding a polypeptide of the invention.

To show that DNA encoding the new NNV coat protein can be used as a vaccine, six 3-month old Balb/c mice were inoculated with 100 μg DNA vaccine in the tibialis anterior muscle or quadriceps muscle. A booster inoculation identical to the initial inoculation was given at week 4. Serum was collected at week 2, 4, 5, 6, and 7. Serum and neutralization titers were determined for each serum sample to evaluate the efficacy of the DNA vaccine. Results show this vaccine strategy produced increased antibody titers (FIG. 4) as well as neutralization titers (one mouse at 6400 titer, one mouse at 3200 titer, two mice at 1600 titer, and two mice at 800 titer) indicating that this DNA vaccine would be efficacious in fish.

Other Embodiments

It is to be understood that while the invention has been described in conjunction with the detailed description thereof, the foregoing description is intended to illustrate and not limit the invention, which is defined by the scope of the appended claims. Other aspects, advantages, and modifications are within the scope of this invention.

What is claimed is:

1. A method of eliciting an antibody response to a nervous necrosis virus in an animal, the method comprising administering to an animal a substantially pure polypeptide comprising an amino acid sequence at least 99% identical to the amino acid sequence of SEQ ID NO:2 in an amount sufficient to elicit an antibody response to the nervous necrosis virus.

2. A method of eliciting an antibody response to a nervous necrosis virus in an animal, the method comprising administering to an animal a substantially pure polypeptide comprising the amino acid sequence of SEQ ID NO:2 in an amount sufficient to elicit an antibody response to the nervous necrosis virus.

3. A method of eliciting an antibody response to a nervous necrosis virus in an animal, the method comprising administering to an animal a substantially pure polypeptide comprising the amino acid sequence of SEQ ID NO:2, with up to 4 conservative amino acid substitutions, in an amount sufficient to elicit an antibody response to the nervous necrosis virus.

4. The method of claim 1, wherein the animal is a fish.

5. The method of claim 2, wherein the animal is a fish.

6. The method of claim 3, wherein the animal is a fish.

7. The method of claim 4, wherein the fish is a grouper.

8. The method of claim 5, wherein the fish is a grouper.

9. The method of claim 6, wherein the fish is a grouper.

10. The method of claim 1, wherein the polypeptide is recombinant.

11. The method of claim 2, wherein the polypeptide is recombinant.

12. The method of claim 3, wherein the polypeptide is recombinant.

* * * * *

```
                              SEQUENCE LISTING

<160> NUMBER OF SEQ ID NOS: 2

<210> SEQ ID NO 1
<211> LENGTH: 1014
<212> TYPE: DNA
<213> ORGANISM: Nervous necrosis virus

<400> SEQUENCE: 1
atggtacgca aaggtgagaa gaaattggca aaacccgcga ccaccaaggc cgcgaatccg      60
caaccccgcc gacgtgctaa caatcgtcgg cgtagtaatc gcactgacgc acctgtgtct     120
aaggcctcga ctgtgactgg atttggacgt gggaccaatg acgtccatct ctcaggtatg     180
tcgagaatct cccaggccgt cctcccagcc gggacaggaa ctgacggata cgttgttgtt     240
gacgcaacca tcgtccccga cctcctgcca cgactgggac acgctgctag aatcttccag     300
cgatacgctg ttgaaacact ggagtttgaa attcagccaa tgtgccccgc aaacacgggc     360
ggtggttacg ttgctggctt cctgcctgat ccaactgaca acgaccacac cttcggcgcg     420
cttcaagcaa ctcgtggtgc agtcgttgcc aaatggtggg aaagcagaac agtccgacct     480
cagtacaccc gcacgctcct ctggacctcg tcgggaaagg agcagcgtct cacgtcacct     540
ggtcggctga tactcctgtg tgtcggcaac aacactgatg tggtcaacgt gtcggtgctg     600
tgtcgctgga gtgttcgact gagcgttcca tctcttgaga cacctgaaga gaccaccgct     660
cccatcatga cacaaggttc cctgtacaac gattccctat ccacaaatga ctccaagtcc     720
atcctcctag gatccacgcc actggacatt gcccctgatg gagcagtctt ccagctggac     780
cgtctgctgt ccattgacta cagccttgga actggagatg ttgaccgtgc tgtttactgg     840
cacctcaaga agtttgctgg aaatgctggc acacctgcag gctggtttcg ctggggcatc     900
tgggacaact tcaacaagac gttcacagat ggcgttgcct actactctga tgagcagccc     960
cgtcaaatcc tgctgcctgt tggcactgtc tgcaccaggg ttgactcgga aaac          1014

<210> SEQ ID NO 2
<211> LENGTH: 338
<212> TYPE: PRT
<213> ORGANISM: Nervous necrosis virus

<400> SEQUENCE: 2

Met Val Arg Lys Gly Glu Lys Lys Leu Ala Lys Pro Ala Thr Thr Lys
 1               5                  10                  15

Ala Ala Asn Pro Gln Pro Arg Arg Arg Ala Asn Asn Arg Arg Arg Ser
            20                  25                  30

Asn Arg Thr Asp Ala Pro Val Ser Lys Ala Ser Thr Val Thr Gly Phe
        35                  40                  45

Gly Arg Gly Thr Asn Asp Val His Leu Ser Gly Met Ser Arg Ile Ser
    50                  55                  60

Gln Ala Val Leu Pro Ala Gly Thr Gly Thr Asp Gly Tyr Val Val Val
65                  70                  75                  80
```

-continued

```
Asp Ala Thr Ile Val Pro Asp Leu Leu Pro Arg Leu Gly His Ala Ala
            85              90              95

Arg Ile Phe Gln Arg Tyr Ala Val Glu Thr Leu Glu Phe Glu Ile Gln
            100             105             110

Pro Met Cys Pro Ala Asn Thr Gly Gly Tyr Val Ala Gly Phe Leu
        115             120             125

Pro Asp Pro Thr Asp Asn Asp His Thr Phe Gly Ala Leu Gln Ala Thr
        130             135             140

Arg Gly Ala Val Val Ala Lys Trp Trp Glu Ser Arg Thr Val Arg Pro
145             150             155             160

Gln Tyr Thr Arg Thr Leu Leu Trp Thr Ser Ser Gly Lys Glu Gln Arg
            165             170             175

Leu Thr Ser Pro Gly Arg Leu Ile Leu Leu Cys Val Gly Asn Asn Thr
            180             185             190

Asp Val Val Asn Val Ser Val Leu Cys Arg Trp Ser Val Arg Leu Ser
            195             200             205

Val Pro Ser Leu Glu Thr Pro Glu Glu Thr Thr Ala Pro Ile Met Thr
    210             215             220

Gln Gly Ser Leu Tyr Asn Asp Ser Leu Ser Thr Asn Asp Ser Lys Ser
225             230             235             240

Ile Leu Leu Gly Ser Thr Pro Leu Asp Ile Ala Pro Asp Gly Ala Val
            245             250             255

Phe Gln Leu Asp Arg Leu Leu Ser Ile Asp Tyr Ser Leu Gly Thr Gly
            260             265             270

Asp Val Asp Arg Ala Val Tyr Trp His Leu Lys Lys Phe Ala Gly Asn
            275             280             285

Ala Gly Thr Pro Ala Gly Trp Phe Arg Trp Gly Ile Trp Asp Asn Phe
    290             295             300

Asn Lys Thr Phe Thr Asp Gly Val Ala Tyr Tyr Ser Asp Glu Gln Pro
305             310             315             320

Arg Gln Ile Leu Leu Pro Val Gly Thr Val Cys Thr Arg Val Asp Ser
            325             330             335

Glu Asn
```